US006461331B1

United States Patent
Van Antwerp

(10) Patent No.: US 6,461,331 B1
(45) Date of Patent: Oct. 8, 2002

(54) DEVICE AND METHOD FOR INFUSION OF SMALL MOLECULE INSULIN MIMETIC MATERIALS

(75) Inventor: William P. Van Antwerp, Valencia, CA (US)

(73) Assignee: MiniMed Inc., Sylmar, CA (US)

( * ) Notice: Subject to any disclaimer, the term of this patent is extended or adjusted under 35 U.S.C. 154(b) by 0 days.

(21) Appl. No.: 09/566,877

(22) Filed: May 8, 2000

Related U.S. Application Data

(60) Provisional application No. 60/135,278, filed on May 21, 1999.

(51) Int. Cl.⁷ ............................................. A61M 37/00
(52) U.S. Cl. ......................................... 604/131; 514/35
(58) Field of Search ................................ 604/131, 141, 604/156; 514/35

(56) References Cited

U.S. PATENT DOCUMENTS

| | | | | |
|---|---|---|---|---|
| 4,360,019 A | * | 11/1982 | Portner et al. | 604/131 |
| 4,573,994 A | | 3/1986 | Fischell et al. | 604/891 |
| 4,685,903 A | | 8/1987 | Cable et al. | 604/154 |
| 5,492,534 A | * | 2/1996 | Athayde et al. | 604/141 |
| 5,652,221 A | * | 7/1997 | Larner et al. | 514/35 |
| 5,676,648 A | | 10/1997 | Henley | 604/20 |
| 5,772,635 A | | 6/1998 | Dastur et al. | 604/131 |
| 5,785,688 A | * | 7/1998 | Joshi et al. | 604/141 |
| 6,165,155 A | * | 12/2000 | Jacobsen et al. | 604/156 |

FOREIGN PATENT DOCUMENTS

| | | |
|---|---|---|
| WO | 9513838 | 5/1995 |
| WO | 9721457 | 6/1997 |

OTHER PUBLICATIONS

Zhang, Bei et al., "Discovery of a Small Molecule Insulin Mimetic with Antidiabetic Activity in Mice", Science, vol. 284, pp. 974–977, XP–002145727, (May 1999).

* cited by examiner

Primary Examiner—Teresa Walberg
Assistant Examiner—Leonid M Fastovsky
(74) Attorney, Agent, or Firm—Gates & Cooper LLP

(57) ABSTRACT

A medication delivery device for delivering a small molecule insulin mimetic material to a body of an individual includes a housing, a reservoir and a controller. The housing contains a driving mechanism, and the reservoir is coupled to the driving mechanism in the housing for holding the small molecule insulin mimetic material to be infused into the body of the individual. The controller controls the driving mechanism to expel the small molecule insulin mimetic material from the reservoir into the body of the individual. Preferably, the medication delivery device is an infusion pump. In particular, the driving mechanism is a syringe type drive actuator, or a gas generator. The driving mechanism may also utilize iontophoresis or passive transdermal delivery. In addition, the driving mechanism is controlled to infuse the small molecule insulin mimetic material in a continuous, near-continuous, intermittent and pulsatile manner. The driving mechanism may also be controlled to deliver discrete, user settable boluses. Preferably, the small molecule insulin mimetic material is L-783,281. Also, the small molecule insulin mimetic material may be an analog of L-783,281. In addition, the small molecule insulin mimetic material may be infused with at least one additional component such as insulin, insulin analogs and insulin related peptides. Preferably, the small molecule insulin mimetic material binds to β sub-units of an insulin receptor site. However, the small molecule insulin mimetic material may bind to α a sub-units of an insulin receptor site. Alternatively, the small molecule insulin mimetic material is a trans-membrane insulin mimetic material that binds to at least one β sub-unit and at least one α a sub-unit of an insulin receptor site.

43 Claims, 3 Drawing Sheets

INSULIN

SMALL MOLECULE

INSULIN BINDING BEGINS THE INTRACELLLULAR SIGNALING PATHWAY LEADING TO GLUCOSE TRANSPORT INTO THE CELL.

SMALL MOLECULE BINDING TO THE β SUBUNITS OF THE GLUCOSE RECEPTOR BEGINS THE INTRACELLULAR SIGNALING PATHWAY LEADING TO GLUCOSE TRANSPORT INTO THE CELL.

DEVICE AND METHOD FOR INFUSION OF SMALL MOLECULE INSULIN MIMETIC MATERIALS

RELATED APPLICATIONS

This application claims priority on U.S. Provisional Application Ser. No. 60/135,278 filed May 21, 1999 and entitled "Device and Method for Infusion of Small Molecule Insulin Mimetic Materials", which is herein specifically incorporated by reference.

FIELD OF THE INVENTION

This invention relates to infusion of small molecule insulin mimetic materials, and in particular embodiments, to continuous, near continuous, intermittent and or basal/bolus infusion of the small molecule mimetic materials for the control of diabetes.

BACKGROUND OF THE INVENTION

Currently, insulin must be provided to people with Type 1 and many with Type 2 diabetes (approximately 40% of patients with Type 2 diabetes use insulin). Traditionally, since it cannot be taken orally, insulin has been injected with a syringe. More recently, use of external infusion pump therapy has been increasing, especially for delivering insulin for diabetics using devices worn on a belt, in a pocket, or the like, with the insulin delivered via a catheter with a percutaneous needle or cannula placed in the subcutaneous tissue. For example, as of 1995, less than 5% of Type I diabetics in the United States were using pump therapy. There are now about 7% of the currently over 900,000 Type I diabetics in the U.S. using insulin pump therapy, and the percentage is now growing at an absolute rate of over 2% each year. Moreover, the number of Type I diabetics is growing at 3% or more per year. In addition, growing numbers of insulin using Type II diabetics are also using external insulin infusion pumps. Physicians have recognized that continuous infusion provides greater control of a diabetic's condition, and are also increasingly prescribing it for patients.

However, administration of insulin by continuous infusion may not resolve all of the individual's needs and could be ineffective for treating some individuals, for example those individuals who are insulin resistant with Type II diabetes. Thus, alternatives to insulin therapy have been sought. Traditionally, oral medications have been used to treat some of the symptoms, but there have been many reports of adverse side-effects and even death. Also, delivery of medication orally suffers from several drawbacks, including, but not limited to, destruction of the medication and delay times until the medication reaches the blood stream of the individual. Therefore, there is the need for alternative treatment regimens that overcome the drawbacks of oral medications and the resistance of some individuals to insulin treatment.

SUMMARY OF THE DISCLOSURE

It is an object of an embodiment of the present invention to provide an a device and method of infusing small molecule insulin mimetic materials using continuous, near continuous, intermittent and or basal/bolus infusion, which obviates for practical purposes, the above mentioned limitations.

According to an embodiment of the invention, a medication delivery device for delivering a small molecule insulin mimetic material to a body of an individual includes a housing, a reservoir and a controller. The housing contains a driving mechanism, and the reservoir is coupled to the driving mechanism in the housing for holding the small molecule insulin mimetic material to be infused into the body of the individual. The controller controls the driving mechanism to expel the small molecule insulin mimetic material from the reservoir into the body of the individual. In preferred embodiments, the medication delivery device is an infusion pump. In particular embodiments, the driving mechanism is a syringe type drive actuator, while in other embodiments it is a gas generator. Alternatively, the small molecule insulin mimetic material is electrically charged and delivered by iontophoresis or passive diffusion through the skin. Preferred embodiments control the driving mechanism to infuse the small molecule insulin mimetic material in a continuous, near-continuous, intermittent and pulsatile manner. Further embodiments control the driving mechanism to deliver discrete, user settable boluses.

In preferred embodiments, the small molecule insulin mimetic material is L-783,281. In other embodiments, the small molecule insulin mimetic material is an analog of L-783,281. The small molecule insulin mimetic material may be infused with at least one additional component such as insulin, insulin analogs and insulin related peptides. In preferred embodiments, the small molecule insulin mimetic material binds to $\beta$ sub-units of an insulin receptor site. In other embodiments, the small molecule insulin mimetic material binds to $\alpha$ sub-units of an insulin receptor site. Alternatively, the small molecule insulin mimetic material is a trans-membrane insulin mimetic material that binds to at least one $\beta$ sub-unit and at least one $\alpha$ sub-unit of an insulin receptor site.

In still other embodiments, the medication delivery device further includes a display and a processor. The processor is connected to the controller and the display, and the processor tracks the infusion and displays information about the infusion the display. In further embodiments, the medication delivery device includes an input from a sensor sensitive to glucose levels in the body, and the input from the sensor is used to control the controller of the medication delivery device. In alternative embodiments, the medication delivery device further includes an input from a sensor sensitive to small molecule insulin mimetic material levels in the body, and the input from the sensor is used to control the controller of the medication delivery device.

In yet other embodiments, the medication delivery device further includes a memory device for storing information about the infusion of the small molecule insulin mimetic material for later recall. In other embodiments, the controller is programmable and/or remotely programmable by a remote programmer.

Other embodiments are directed to methods of infusing a small molecule insulin mimetic material into the body of an individual.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
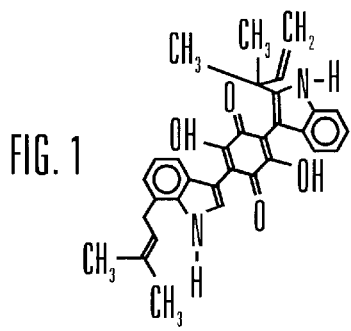
FIG. 1 is a drawing of the chemical structure of a small molecule insulin mimetic material for use with infusion in accordance with an embodiment of the present invention.

As shown in the drawings for purposes of illustration, the invention is embodied in an infusion pump for infusing molecule insulin mimetic materials into the body of an individual to treat conditions related to diabetes. Preferred embodiments infuse the molecule insulin mimetic material on a continuous, intermittent or near continuous basis. In alternative embodiments, the molecule insulin mimetic material may be infused in a pulsed manner or augmented with boluses for greater control over blood glucose levels in the body. In preferred embodiments of the present invention, the molecule insulin mimetic material is administered through subcutaneous or intra-peritoneal human tissue. However, still further embodiments may be administered in other types tissue, such as muscle, lymph, organ tissue, veins, arteries or the like, infused by IV or inhalation, and used in animal tissue. In addition, the small molecule insulin mimetic material may be used to treat Type I and Type II diabetes, since it provides an alternative insulin receptor activator that would work for both types of diabetes.

Figure 2B:
FIG. 2(b) is an illustrative drawing of an insulin molecule.
Figure 2C:
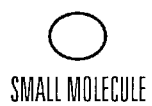
FIG. 2(c) is an illustrative drawing of a small molecule insulin mimetic material similar to that shown in FIG. 1
Figure 2A:
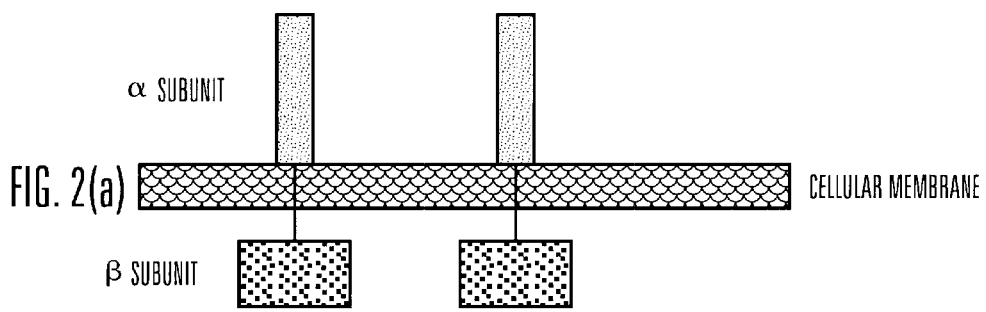
FIG. 2(a) is an illustrative drawing of an insulin receptor site having α and β sub-units that have not been activated to transport glucose.
Figure 3:
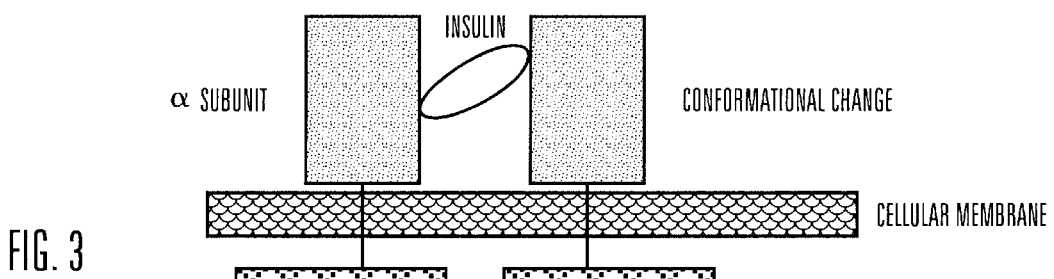
FIG. 3 is an illustrative drawing of insulin bound to the α sub-units of the insulin receptor site to facilitate glucose transport across the cellular membrane in accordance with an embodiment of the present invention.

FIGS. 2–3 illustrate the action of a human insulin receptor site when binding with insulin to facilitate glucose transport across the cellular membrane. As shown in FIG. 2(a), the insulin receptor site includes two a sub-units on the exterior of the cellular membrane. Each α sub-unit is connected with a corresponding β sub-unit on the other side of the cellular membrane. If no insulin is present, the insulin receptor site does not transport glucose across the cellular membrane. However, as shown in FIG. 3, when an insulin molecule binds to the a sub-units of the insulin receptor site, there is a conformal change to the a sub-units and the β sub-units that begins the intracellular signaling pathway to facilitate glucose transport across the cellular membrane. Thus, insulin is important and required for the proper metabolism of glucose by the cells of an individual's body. If the body does not produce insulin, or is resistant to insulin, additional insulin must be provided to the individual. Alternatively, an insulin resistant individual may take other medications to ameliorate the body's insulin resistance. However, in all cases, the goal is to provide or improve the body's ability to use insulin to activate the insulin receptor site. Preferably, additional insulin and/or medication is provided to an individual via an infusion pump (see FIG. 6) to maximize the ability to control a diabetics condition. Infusion helps to avoid many of the highs and lows experienced by diabetics using sporadic injections or taking pills at periodic intervals throughout the day.

Figure 8:
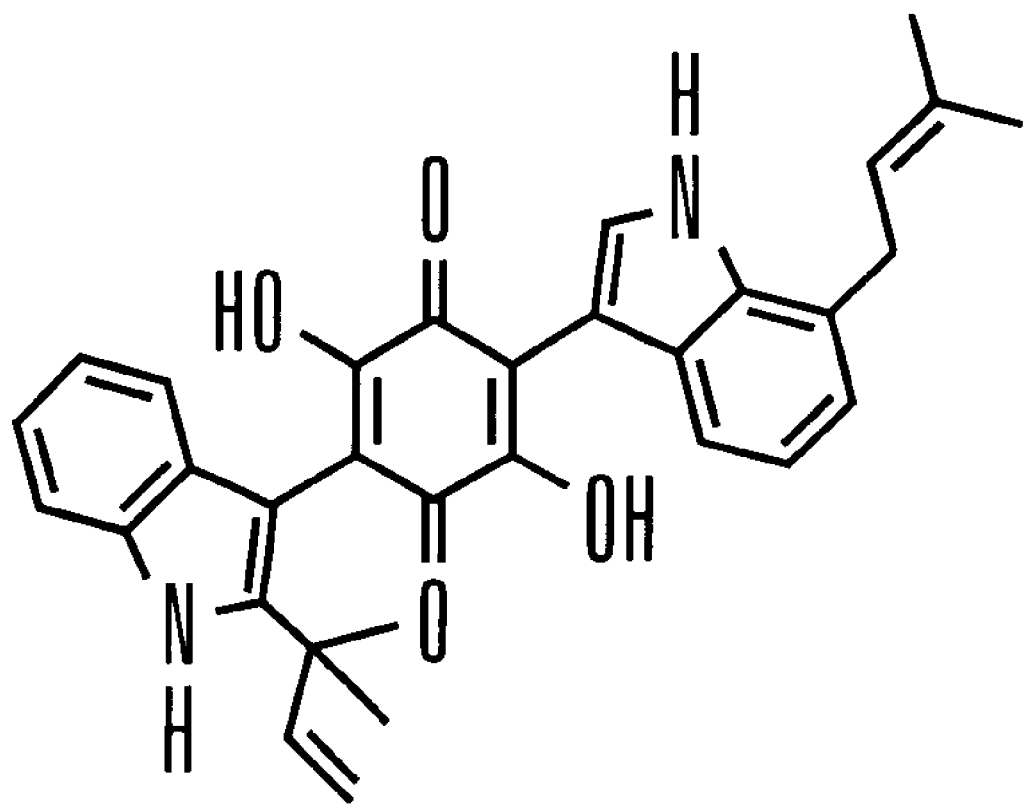
FIG. 8 is a drawing of the chemical structure of a small molecule insulin mimetic material L-783,281 for use with infusion in accordance with an embodiment of the present invention.

Recently, a compound L-783,281 (see FIG. 8), which is a non-peptide fungal metabolite from a fungal extract (Psuedomassaria sp), was found to reduce blood glucose levels when orally administered to mice. The L-783,281 molecule activated the human insulin receptor tyrosine kinase to mimic insulin, and thus mimicked the properties and capabilities of insulin. The article describing this material and its properties, "Discovery of a Small Molecule Mimetic with Antidiabetic Activity in Mice", Zhang et al. SCIENCE Vol. 284, pages 974–977 (May 7, 1999), is specifically incorporated by reference herein. A similar variation of the small molecule insulin mimetic material in accordance with an embodiment of the present invention is shown in FIG. 1. Although the molecule shown in FIG. 1 is preferred for infusion delivery, other mimetic materials and analogs of the material shown in FIG. 1 that have comparable properties may be used.

Figure 4:
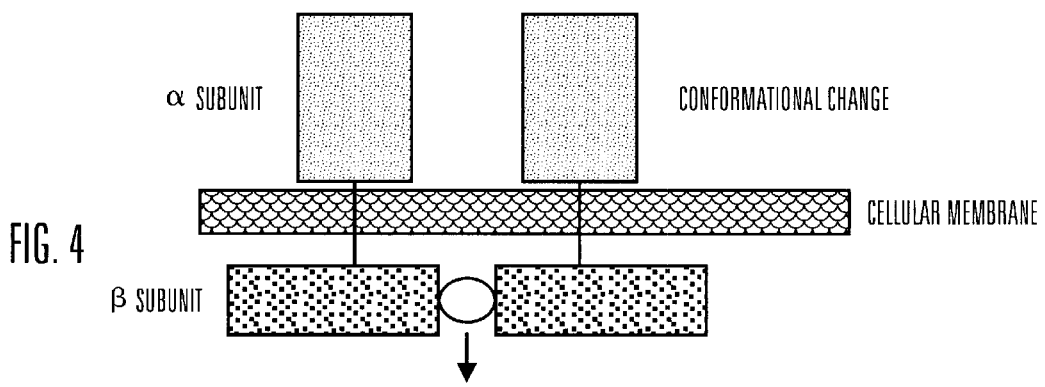
FIG. 4 is an illustrative drawing of a small molecule insulin mimetic material that is bound to the β sub-units of the insulin receptor site to facilitate glucose transport across the cellular membrane in accordance with another embodiment of the present invention.

As shown in FIG. 4, the small molecule insulin mimetic materials (such as shown in FIG. 1) binds to the β sub-units rather than the α sub-units by passing through the cellular membrane. Once bound to the β sub-units of the insulin receptor site, it causes the insulin receptor site to form the same intracellular signaling pathway to facilitate transport of glucose across the cellular membrane. Thus, for the first time, materials other than insulin are becoming available to provide an alternate way of activating the insulin receptor site and facilitating transport of glucose to a body's cells. Currently, these compounds are planned to be delivered by oral administration.

Although the oral administration of an insulin mimetic material, as described by the article, would represent a significant improvement over the delivery of insulin for certain diabetic patients (e.g., since insulin can not be administered orally). Oral administration of a medication would still suffer from several drawbacks. For instance, oral administration is less precise, since varying amounts of the medication reach the blood stream of the user due to the digestive effects and absorption. In addition, there are delays associated with oral administration as the material passes through the digestive system. Also, since this materials act in a manner similar to insulin, very slow time release following oral administration or frequent oral administrations of small molecule mimetic materials similar to that shown in FIG. 1 will be required to effectively treat the diabetic condition.

Figure 7:
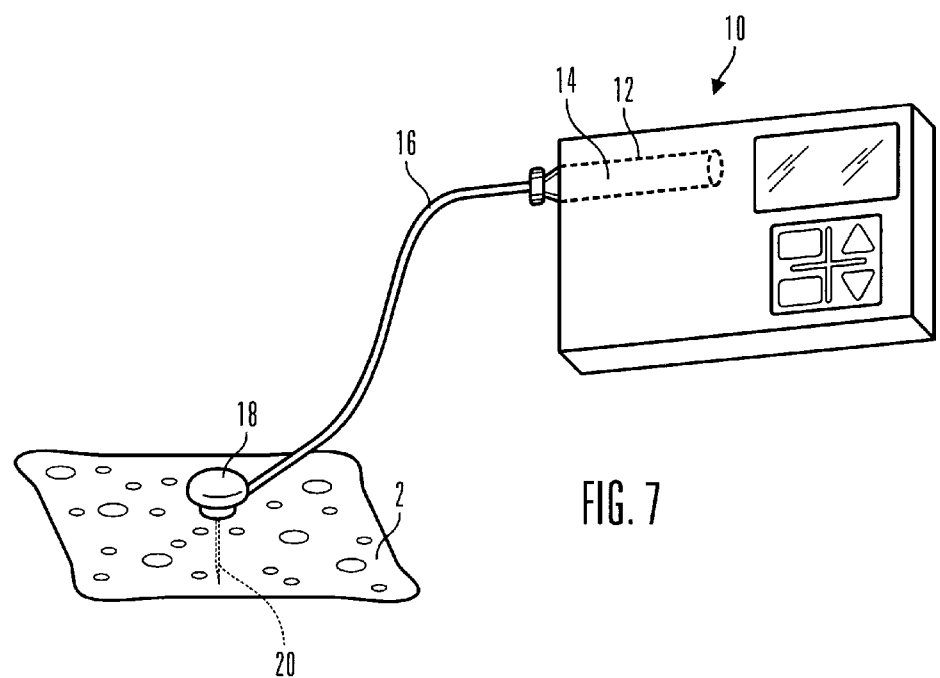
FIG. 7 is a perspective view of an infusion pump to infuse a small molecule insulin mimetic material into subcutaneous tissue in accordance with an embodiment of the present invention.

Thus, as shown in FIG. 7, it is preferable to infuse a small molecule insulin mimetic material into the body of an individual as an alternative, and/or in addition to, insulin. Preferred embodiments would utilize an external infusion pump 10 containing a reservoir 12 that holds the small molecule insulin mimetic material 14 (such as shown in FIG. 1) that is infused through a tube 16 into a set 18 with a cannula 20 placed in the subcutaneous tissue of an individual 2. In alternative embodiments, the small molecule insulin mimetic material may be used in conjunction with automated or semi-automated medication infusion pumps of the external or implantable type as described in U.S. Pat. Nos. 4,562,751; 4,678,408; 4,685,903 or U.S. Pat. No. 4,573,994. Alternative embodiments may utilize external basal infusers or disposable infusion devices to deliver the small molecule insulin mimetic material. Typical infusers can use elastomeric members, gas generators, pressurized chambers or the like to infuse the small molecule insulin mimetic material. Preferred embodiments utilize continuous, near continuous, pulsatile or intermittent infusion to provide the small molecule insulin mimetic material over a period of time. For instance, the infusion pump may provide the small molecule insulin mimetic material as a basal infusion to activate the insulin receptor. In alternative embodiments, the infusion pumps may include a bolus feature to provide discrete amounts of the small molecule insulin mimetic material at any desired point in time, such as just before a meal or prior to disconnecting from the infusion pump. Other features that may be incorporated into the infusion pump that provides the small molecule insulin mimetic material to an individual are described in U.S. patent application Ser. No. 09/334,858 (PCT/US99/18977 published as WO 00/10628) filed on Jun. 16, 1999 and is entitled "EXTERNAL INFUSION DEVICE WITH REMOTE PROGRAMMING, BOLUS ESTIMATOR AND/OR VIBRATION ALARM CAPABILITIES," which is herein incorporated by reference.

Still further embodiments may electrically charge the small molecule insulin mimetic material and use an infusion device that incorporates iontophoresis. Other embodiments may utilize other electrically assisted delivery of the small molecule insulin mimetic material. In addition, passive trans-dermal delivery utilizing, for example, but not limited to, ultrasonic delivery, chemical enhancers (such as DMSO or the like) may be used. Also, micro-poration of the skin to increase the permeability of the skin to transmission of the small molecule insulin mimetic material.

Alternative embodiments may utilize inhalation, either continuously or on an intermittent basis, to quickly provide the small molecule insulin mimetic material to the mucus membranes of the mouth, nose and/or lung tissue for quicker absorption than can be achieved with oral administration. In further embodiments, the small molecule insulin mimetic material may be encapsulated or suspended in a material that allows for first order kinetic delivery of the small molecule insulin mimetic material. For instance, a single injection could be placed under the skin and the medication would be continuously released over time.

In addition, further embodiments may use a sensor sensitive to either blood glucose levels and/or the small molecule insulin mimetic material levels to provide information to the infusion pump. In one alternative, the sensor information is used to provide an estimate to the individual on how to alter infusion of the small insulin mimetic material, while in another alternative, the sensor is used as part of a closed-loop system to infuse the small molecule insulin mimetic material over time. The small molecule insulin mimetic material may be more easily detected than insulin (e.g., by fluorescence, chemical, electro-optical techniques or the like) due to its unique chemistry and not be found elsewhere in the body as a naturally occurring substance. Also, the small molecule insulin mimetic material would not tend to be deactivated and break up like insulin.

Preferred embodiments infuse the small molecule insulin mimetic material in shown in FIG. 1. However, alternative embodiments, may infuse analogs of the small molecule insulin mimetic material shown in FIG. 1 that have comparable properties. Also, some embodiments may infuse the small molecule insulin mimetic material with insulin peptides to provide a infusion that closely approximates the delivery of insulin and its other constitute component peptides. Still other embodiments of the small molecule insulin mimetic material may be infused with insulin (and/or insulin analogs) to provide a balanced infusion that augments the effects of insulin. An advantage to the use of small molecule insulin mimetic materials is that the pharmokinetic properties of the particular molecule can be more reliably controlled so that an infusion regimen could be closely tailored to the individual's needs. For instance, the small molecule insulin mimetic material may only activate the insulin receptor sites in the individual's body and would not induce other insulin activated effects or conditions. In preferred embodiments, the small molecule insulin mimetic material is suspended in a buffering solution and infused directly into the body of the individual. However, in alternative embodiments, the small molecule insulin mimetic material may be micro-encapsulated to protect the material prior to infusion. For instance, this may be necessitated by storage conditions or to prevent reactions with other materials mixed into the liquid to be infused.

Figure 5:
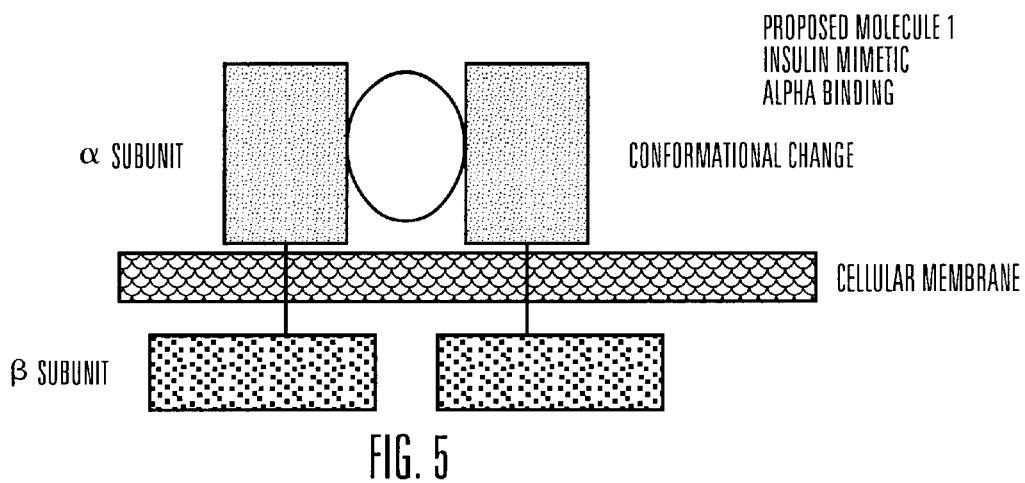
FIG. 5 is an illustrative drawing of a molecule insulin mimetic material bound to the α sub-units of the insulin receptor site to facilitate glucose transport across the cellular membrane in accordance with still another embodiment of the present invention.

FIG. 5 illustrates an alternative embodiment of an insulin mimetic material. This material behaves (i.e., mimics) in a manner that is similar to insulin, since it will bind to the a sub-units of the insulin receptor site to facilitate the transport of glucose across the cellular membrane. An advantage of this molecule design is that it does not need to pass through the cellular membrane to activate the insulin receptor site. This would permit the use of an insulin mimetic material that is larger than the small molecule materials that must pass through the cellular membranes.

Figure 6:
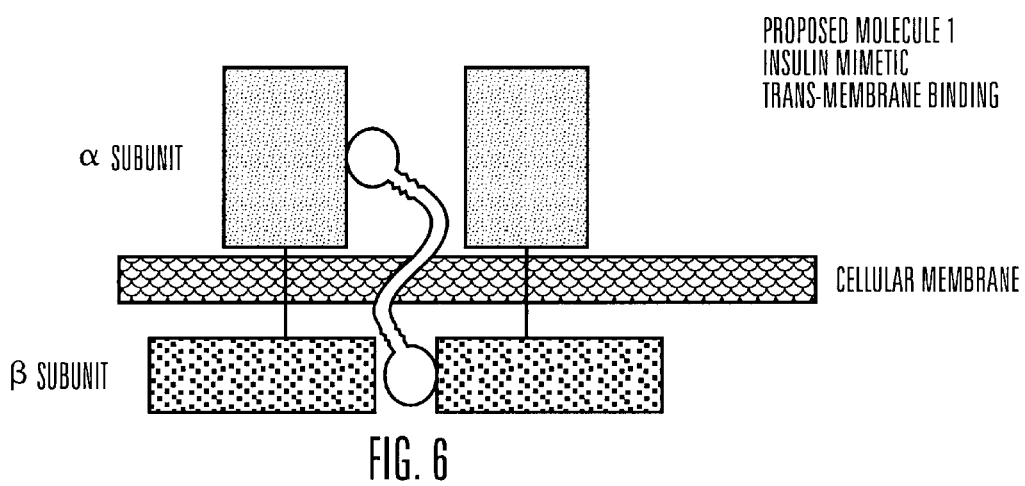
FIG. 6 is an illustrative drawing of a small molecule insulin mimetic trans-membrane material that is bound to an α sub-unit and β sub-unit of the insulin receptor site to facilitate glucose transport across the cellular membrane in accordance with yet another embodiment of the present invention.

FIG. 6 illustrates another alternative embodiment of an insulin mimetic material. This material has a portion that that passes through the cellular membrane and binds with at least one of the β sub-units, while the portion that does not pass through the cellular membrane binds to at least one of the a sub-units of the insulin receptor site to facilitate the transport of glucose across the cellular membrane. Although FIG. 6 shows the proposed trans-membrane molecule binding to particular sub-units, alternative embodiments may be bound to the mirror sub-units or all of the sub-units.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medication delivery device for delivering a small molecule insulin mimetic material to a body of an individual, the device comprising:

a housing containing a driving mechanism;

a reservoir that is coupled to the driving mechanism in the housing for holding the small molecule insulin mimetic material to be infused into the body of the individual; and a controller to control the driving mechanism to expel the small molecule insulin mimetic material from the reservoir into the body of the individual.

2. The device according to claim 1, wherein the medication delivery device is an infusion pump.

3. The device according to claim 2, wherein the driving mechanism is a syringe type drive actuator.

4. The device according to claim 2, wherein the driving mechanism is a gas generator.

5. The device according to claim 1, wherein the driving mechanism utilizes iontophoresis.

6. The device according to claim 1, wherein the driving mechanism is controlled to infuse the small molecule insulin mimetic material from a mode selected from the group consisting essentially of continuous, near-continuous, intermittent and pulsatile.

7. The device according to claim 1, wherein the driving mechanism is controlled by the controller to deliver discrete, user settable boluses.

8. The device according to claim 1, wherein the small molecule insulin mimetic material is L-783,281.

9. The device according to claim 1, wherein the small molecule insulin mimetic material is an analog of L-783,281.

10. The device according to claim 1, wherein the small molecule insulin mimetic material is infused with insulin related peptides.

11. The device according to claim 1, wherein the small molecule insulin mimetic material is infused with at least one additional component selected from the group consisting essentially of insulin, insulin analogs and insulin related peptides.

12. The device according to claim 1, wherein the small molecule insulin mimetic material binds to β sub-units of an insulin receptor site.

13. The device according to claim 1, wherein the small molecule insulin mimetic material binds to α sub-units of an insulin receptor site.

14. The device according to claim 1, wherein the small molecule insulin mimetic material binds to at least one β sub-unit and at least one α sub-unit of an insulin receptor site.

15. The device according to claim 14, wherein the small molecule insulin mimetic material is a trans-membrane insulin mimetic material.

16. The device according to claim 1, further including a display and a processor, wherein the processor is connected to the controller and the display, and wherein the processor tracks the infusion and displays information about the infusion on the display.

17. The device according to claim 1, further including an input from a sensor sensitive to glucose levels in the body, and wherein the input from the sensor is used to control the controller of the medication delivery device.

18. The device according to claim 1, further including an input from a sensor sensitive to small molecule insulin mimetic material levels in the body, and wherein the input from the sensor is used to control the controller of the medication delivery device.

19. The device according to claim 1, further including a memory device for storing information about the infusion of the molecule insulin mimetic material for later recall.

20. The device according to claim 1, wherein the controller is programmable.

21. A method of delivering a small molecular insulin mimetic material to a body of an individual, the method comprising the steps of:

providing a medication delivery device with a driving mechanism;

holding the small molecule insulin mimetic material to be infused into the body of the individual in a reservoir;

coupling the reservoir to the driving mechanism; and controlling the driving mechanism to expel the small molecule insulin mimeric material from the reservoir into the body of the individual.

22. The method according to claim 21, wherein the medication delivery device is an infusion pump, and the driving mechanism of the infusion pump expels the small molecule insulin mimetic material.

23. The method according to claim 22, wherein the driving mechanism uses a syringe type drive actuator to expel the small molecule insulin mimetic material.

24. The method according to claim 22, wherein the driving mechanism uses a gas generator to expel the small molecule insulin mimetic material.

25. The method according to claim 21, wherein the driving mechanism uses iontophoresis to expel the small molecule insulin mimetic material.

26. The method according to claim 21, further comprising controlling the driving mechanism to infuse the small molecule insulin mimetic material from a mode selected from the group consisting essentially of continuous, near-continuous, intermittent and pulsatile.

27. The method according to claim 21, further comprising controlling the driving mechanism to deliver discrete, user settable boluses.

28. The method according to claim 21, wherein the small molecule insulin mimetic material is L-783,281.

29. The method according to claim 21, wherein the small molecule insulin mimetic material is an analog of L-783,281.

30. The method according to claim 21, wherein the small molecule insulin mimetic material is infused with insulin related peptides.

31. The method according to claim 21, wherein the small molecule insulin mimetic material is infused with at least one additional component selected from the group consisting essentially of insulin, insulin analogs and insulin related peptides.

32. The method according to claim 21, wherein the small molecule insulin mimetic material binds to β sub-units of an insulin receptor site.

33. The method according to claim 21, wherein the small molecule insulin mimetic material binds to α sub-units of an insulin receptor site.

34. The method according to claim 21, wherein the small molecule insulin mimetic material binds to at least one β sub-unit and at least one α sub-unit of an insulin receptor site.

35. The method according to claim 34, wherein the small molecule insulin mimetic material is a trans-membrane insulin mimetic material.

36. The method according to claim 21, further including using a processor to track the infusion and to display information about the infusion a display.

37. The method according to claim 21, further including using an input from a sensor sensitive to glucose levels in the body, and using the input from the sensor to control the medication delivery device.

38. The method according to claim 21, further including using an input from a sensor sensitive to small molecule insulin mimetic material levels in the body, and using the input from the sensor to control the medication delivery device.

39. The method according to claim 21, further including using a memory device for storing information about the infusion of the small molecule insulin mimetic material for later recall.

40. The method according to claim 21, further comprising programming the medication delivery device.

41. The device according to claim 40, further comprising remotely programming the medication delivery device.

42. A medication delivery device for delivering a small molecule insulin mimetic material to a body of an individual, the device comprising:

a housing containing a driving mechanism;

a reservoir that is coupled to the driving mechanism in the housing for holding the small molecule insulin mimetic material to be infused into the body of the individual;

a controller to control the driving mechanism to expel the small molecule insulin mimetic material from the reservoir into the body of the individual; and an input from a sensor sensitive to small molecule insulin mimetic material levels in the body, and wherein the input from the sensor is used to control the controller of the medication delivery device.

43. The device according to claim 42, wherein the small molecule insulin mimetic material is infused with at least one a additional component selected from the group consisting essentially of insulin, insulin analogs, and insulin related peptides.

* * * * *